(12) United States Patent
Zheng

(10) Patent No.: US 9,238,776 B2
(45) Date of Patent: Jan. 19, 2016

(54) LIQUID CRYSTAL BLUE PHASE

(75) Inventor: Zhigang Zheng, Shanghai (CN)

(73) Assignee: East China University of Science and Technology, Shanghai (CN)

( * ) Notice: Subject to any disclaimer, the term of this patent is extended or adjusted under 35 U.S.C. 154(b) by 115 days.

(21) Appl. No.: 14/000,207

(22) PCT Filed: Mar. 22, 2012

(86) PCT No.: PCT/CN2012/072798
§ 371 (c)(1), (2), (4) Date: Aug. 17, 2013

(87) PCT Pub. No.: WO2013/139020
PCT Pub. Date: Sep. 26, 2013

(65) Prior Publication Data
US 2013/0337197 A1 Dec. 19, 2013

(51) Int. Cl.
| C09K 19/02 | (2006.01) |
|---|---|
| C09K 19/54 | (2006.01) |
| C09K 19/58 | (2006.01) |
| C09K 19/34 | (2006.01) |
| C09K 19/20 | (2006.01) |
| C09K 19/22 | (2006.01) |
| C09K 19/24 | (2006.01) |

(Continued)

(52) U.S. Cl.
CPC ............ *C09K 19/54* (2013.01); *C09K 19/0275* (2013.01); *C09K 19/3486* (2013.01); *C07D 271/10* (2013.01); *C09K 19/02* (2013.01); *C09K 19/20* (2013.01); *C09K 19/22* (2013.01); *C09K 19/24* (2013.01); *C09K 19/26* (2013.01); *Y10T 428/10* (2015.01)

(58) Field of Classification Search
CPC .............. C09K 19/34; C09K 19/3405; C09K 19/3486; C09K 19/54; C09K 2019/586; C09K 19/02; C09K 19/0275; C09K 19/20; C09K 19/22; C09K 19/24; C09K 19/26; C09K 19/28; C09K 19/586; C09K 2219/03; Y10T 428/10
See application file for complete search history.

(56) References Cited

U.S. PATENT DOCUMENTS

| 6,863,841 B2 | 3/2005 | Kirsch et al. |
| 7,871,539 B2 | 1/2011 | Takaku et al. |
| 2003/0166943 A1 | 9/2003 | Kirsch et al. |

(Continued)

FOREIGN PATENT DOCUMENTS

| CN | 1934222 A | 3/2007 |
| CN | 102443402 A | 5/2012 |

(Continued)

OTHER PUBLICATIONS

International Search Report and Written Opinion for PCT/CN2012/072798 dated Jan. 3, 2013.

(Continued)

*Primary Examiner* — Shean C Wu
(74) *Attorney, Agent, or Firm* — Pepper Hamilton LLP

(57) ABSTRACT

Methods of forming a liquid crystal blue phase from composite materials having a chiral nematic liquid crystal host and a bent-shape molecule are described. The stable temperature range of the liquid crystal blue phase may be improved by controlling the thickness of the composite materials. For example, a given composition may have a maximum stable temperature range for the liquid crystal blue phase at about 1 μm.

23 Claims, 1 Drawing Sheet

(51) Int. Cl.
  *C09K 19/26* (2006.01)
  *C07D 271/10* (2006.01)

(56) References Cited

U.S. PATENT DOCUMENTS

2005/0185131 A1* 8/2005 Miyachi et al. ............... 349/167
2012/0138853 A1  6/2012 Kubota et al.
2013/0187091 A1* 7/2013 Zheng ..................... 252/299.01

FOREIGN PATENT DOCUMENTS

JP    2004002288 A    1/2004
JP    2012131987 A    7/2012
WO   WO 2012/074081 A1  6/2012

OTHER PUBLICATIONS

Cao et al., Lasing in a three-dimensional photonic crystal of the liquid crystal blue phase II, *Nat Mater.* (Oct. 2002), 1(2):111-113 (Abstract).
Chen et al., Hysteresis Effects in Blue-Phase Liquid Crystals, *Journal of Display Technology* (2010), 6(8):318-322 (Abstract).
Chen et al., Molecular Dynamics Simulation of a Phenylene Polymer. 1. Poly(phenylene oxide), *Macromolecules* (Apr. 1994), 27(8):2087-2091 (Abstract).
Cheung et al., Calculation of the rotational viscosity of a nematic liquid crystal, *Chemical Physics Letters* (Apr. 15, 2002), 356:140-146.
Coles et al., Liquid crystal 'blue phases' with a wide temperature range, *Nature* (Aug. 18, 2005), 436:997-1000 (Abstract).
De Gennes et al., The Physics of Liquid Blue Crystals, Clarendon Press, Second Edition (Dec. 1, 1993), pp. 1-616 (Abstract).
Ge et al., Modeling of Blue Phase Liquid Crystal Displays, *Journal of Display Technology* (2009), 5(7):250-256 (Abstract).
Ge et al., Electro-optics of polymer-stabilized blue phase liquid crystal displays, *Appl. Phys. Lett.* (Mar. 10, 2009), 94(10):101104-101106 (Abstract).
Hisakado et al., Large Electro-optic Kerr Effect in Polymer-Stabilized Liquid-Crystalline Blue Phases, *Advanced Materials* (Oct. 20, 2004), 17(1):96-98 (Abstract).
Hong et al., Thickness Dependence of Blue Phase Transition Behavior of Chiral Nematic Liquid Crystal, *Molecular Crystals and Liquid Crystals* (Oct. 5, 2009), 511(1):248-254.

Jiao et al., Low voltage and high transmittance blue-phase liquid crystal displays with corrugated electrodes, *Appl. Phys. Lett.* (Jan. 4, 2010), 96(1):011102-011104 (Abstract).
Kikuchi et al., Polymer-stabilized liquid crystal blue phases, *Nature Materials* (Sep. 2, 2002), 1:64-68 (Abstract).
Kikuchi et al., Liquid Crystalline Blue Phases, *Structure and Bonding* (2008), 128:99-117 (Abstract).
Li et al., Polarization independent adaptive microlens with a blue-phase liquid crystal, *Optics Express* (Apr. 25, 2011), 19(9):8045-8050.
Li et al., Transflective display using a polymer-stabilized blue-phase liquid crystal, *Optics Express* (Aug. 2, 2010), 18(16):16486-16491.
Lin et al., Polarizer-free and fast response microlens arrays using polymer-stabilized blue phase liquid crystal, *Appl. Phys. Lett.* (Mar. 15, 2010), 96(11):113505:113507 (Abstract).
Lu et al., Electrically switched color with polymer-stabilized blue-phase liquid crystals, *Optics Letters* (Feb. 11, 2010), 35(4):562-564 (Abstract).
Nakata et al., Blue phases induced by doping chiral nematic liquid crystals with nonchiral molecules, *Phys Rev E Stat Nonlin Soft Matter Phys.* (Oct. 2003), 68(4, Part 1):041710 (Abstract).
Rao et al., Low voltage blue-phase liquid crystal displays, *Appl. Phys. Lett.* (Dec. 7, 2009), 95(23):231101-231103 (Abstract).
Yan et al., High-efficiency and fast-response tunable phase grating using a blue phase liquid crystal, *Optics Letters* (Apr. 13, 2011), 36(8):1404-1406 (Abstract).
Yokoyama et al., Laser Emission from a Polymer-Stabilized Liquid-Crystalline Blue Phase, *Advanced Materials* (Dec. 5, 2005), 18(1):48-51 (Abstract).
Yoshida et al., Nanoparticle-Stabilized Cholesteric Blue Phases, *Appl. Phys. Express* (Nov. 27, 2009), 2:121501-121503 (Abstract).
Yoshizawa et al., A blue phase observed for a novel chiral compound possessing molecular biaxiality, *Journal of Materials Chemistry* (Jul. 11, 2005), 15(32):3285-3290 (Abstract).
Zheng et al., The Liquid crystal blue phase induced by bent-shaped molecules with different terminal chain lengths, *New Journal of Physics* (Jun. 20, 2011), 13:063037-063044.
Zheng et al., Wide blue phase range of chiral nematic liquid crystal doped with bent-shaped molecules, *New Journal of Physics* (Nov. 10, 2010), 12:113018-113028.
Zheng et al., Molecular dynamics of the interfacial properties of partially fluorinated polymer dispersed liquid crystal gratings, *Journal of Physics D: Applied Physics* (Nov. 4, 2008), 41(23) (Abstract).
Wang et al., Blue phase liquid crystals induced by bent-shaped molecules based on 1,3,4-oxadiazole derivatives, *Liquid Crystals* (Jan. 2012), 39(1):99-103.

* cited by examiner

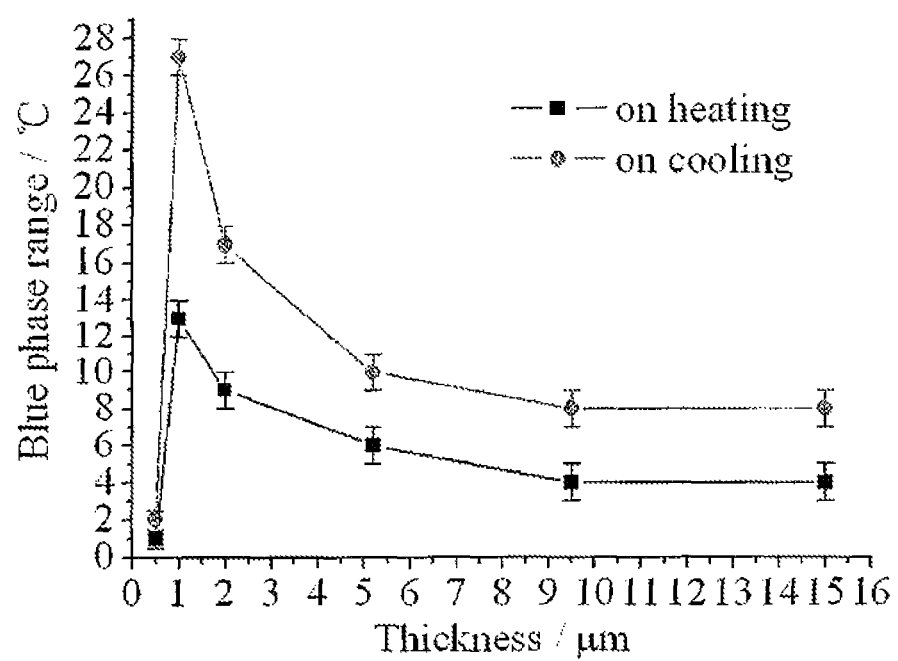

LIQUID CRYSTAL BLUE PHASE

CROSS-REFERENCE TO RELATED APPLICATIONS

This application is a U.S. national stage filing under 35 U.S.C. §371 of International Application No. PCT/CN2012/072798, entitled "A Novel Design for Bent-Shaped Molecules Stabilized Liquid Crystal Blue Phase", filed on Mar. 22, 2012, which is incorporated herein by reference in its entirety.

BACKGROUND

The liquid crystal blue phase is a thermotropic mesophase, usually existing between the isotropic phase and the chiral nematic phase that was first identified in an 1888 report describing the melting behavior of cholesteryl benzoate. The report noted that the substance briefly turned blue as it changed from clear to cloudy upon cooling. The structure of the liquid crystal blue phase is formed by double-twisted cylinders, which are self-assembled and form three dimensional cubic lattices. Such an arrangement endows the liquid crystal blue phase with special properties, such as optical isotropy, tunable reflection of circular polarized light with certain wavelengths, microsecond response, etc. These properties enable many potential applications of liquid crystal blue phase including high efficiency flat panel displays, fast response optical devices and improved laser techniques. Practical applications using the liquid crystal blue phase have been limited by their stability only in a narrow temperature range (typically about 1° K).

SUMMARY

This disclosure is not limited to the particular systems, devices and methods described, as these may vary. The terminology used in the description is for the purpose of describing the particular versions or embodiments only, and is not intended to limit the scope. While various compositions and methods are described in terms of "comprising" various components or steps (interpreted as meaning "including, but not limited to"), the compositions and methods can also "consist essentially of" or "consist of" the various components and steps, and such terminology should be interpreted as defining essentially closed-member groups.

Embodiments describe a composite material which forms a stable liquid crystal blue phase, methods for preparing the liquid crystal blue phase, and devices comprising the composite material.

In an embodiment, a composite material comprises a chiral nematic liquid crystal host and at least one bent-shape compound, wherein the composite material has a liquid crystal blue phase that may have a stable temperature range of at least about 5° C. In some embodiments, the composite material has a thickness of about 0.5 μm to about 2 μm. In some embodiments, the bent-shape compound has a structure of formula (I): wherein $R_1$ and $R_2$ are each independently selected from halogens and aliphatic hydrocarbons comprising 1 to 15 carbons; $Ar_1$, $Ar_2$, $Ar_3$, $Ar_4$ and $Ar_5$, are each independently selected from homocyclic aromatics, substituted homocyclic aromatics, heterocyclic aromatics, substituted heterocyclic aromatics, polycyclic aromatics, and substituted polycyclic aromatics; $X_1$ and $X_2$ are each independently selected from $CH_2$, O, NH, and S; and $Y_1$ and $Y_2$ are each independently selected from C=O, C=$CH_2$, C=NH, and C=S.

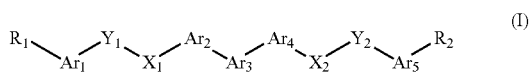

In an embodiment, a composite material comprising a chiral nematic liquid crystal host and at least one bent-shaped compound has a liquid crystal blue phase and a thickness of about 0.5 μm to about 2 μm.

In an embodiment, a method of preparing a liquid crystal blue phase comprises: providing a thin-film comprising a mixture of a chiral nematic liquid crystal host and at least one bent-shape compound; heating the thin-film; and cooling the thin-film to produce a liquid blue phase, wherein the liquid crystal blue phase has a stable temperature range of at least about 5° C.

In an embodiment, a method of preparing a liquid crystal blue phase comprises: providing a thin-film comprising a mixture of a chiral nematic liquid crystal host and at least one bent-shape compound; heating the thin-film; and cooling the heated thin-film, to produce a liquid blue phase, wherein the thin-film has a thickness of about 0.5 μm to 2 μm.

In an embodiment, a display device comprises a composite material, wherein the composite material comprises a chiral nematic liquid crystal host and at least one bent-shape compound. In these embodiments, the display device may be a blue phase mode liquid crystal display with improved fabrication costs relative to traditional liquid crystal displays.

DESCRIPTION OF FIGURE

FIG. 1 is a plot of blue phase temperature range versus composite material thickness.

DETAILED DESCRIPTION

Described herein is a composite material which forms a liquid crystal blue phase, methods for preparing the liquid crystal blue phase, and devices comprising the composite material. In some embodiments, the liquid crystal blue phase of the composite material may have an improved temperature range of stability compared to typical ranges of only a few degrees. In some embodiments, the improved range is dependent on the thickness of the film. The improved range of stability for the liquid crystal blue phase may facilitate the use of the composite material in, for example, display devices.

In an embodiment, a composite material comprising a chiral nematic liquid crystal host and at least one bent-shaped compound has a liquid crystal blue phase with a stable temperature range of at least about 5° C.

In an embodiment, a composite material comprising a chiral nematic liquid crystal host and at least one bent-shaped compound has a liquid crystal blue phase and a thickness of about 0.5 μm to about 2 μm.

In some embodiments, the liquid crystal blue phase of the composite material may have a stable temperature range of at least about 2° C., about 5° C., about 10° C., about 15° C., or about 20° C. In some embodiments, the liquid crystal blue phase may have a stable temperature range of about 10° C. to about 30° C. Specific examples of stable temperature ranges include about 5° C., about 10° C. about 20° C., about 40° C., about 60° C., and ranges between any two of these temperature ranges (for example, about 20° C. to about 60° C.). In some embodiments, the liquid crystal blue phase of the composite material may have stable temperature range that may be improved by adjusting the thickness of the composite material (FIG. 1). In these embodiments, the stable temperature range may vary based on the composition of composite material.

In embodiments, the composite material may have a thickness of about 0.25 µm to about 15 µm. In some embodiments, the composite material may have a thickness of about 0.5 µm to about 2 µm. In some embodiments, the composite material may have a thickness of about 0.75 µm to about 1.5 µm. In some embodiments, the composite material may have a thickness of about 1 µm. Specific examples of thicknesses include about 0.25 µm, about 0.75 µm, about 1 µm, about 1.5 µm, about 2 µm, about 4 µm, about 10 µm, and ranges between any two of these thicknesses (for example, about 0.75 µm to about 1.5 µm). In some embodiments the thickness of composite material may be modified to improve the stable temperature range of the liquid crystal blue phase. In these embodiments, the thickness may vary based on the composition of the composite material.

In some embodiments, the bent-shape compound may be present in the composite material at about 5 weight percent to about 20 weight percent. In some embodiments, the bent-shape compound may be present in the composite material at about 7 weight percent. Specific examples of weight percent include about 5 weight percent, about 8 weight percent, about 11 weight percent, about 14 weight percent, about 17 weight percent, about 20 weight percent, and ranges between any two of these thicknesses (for example, about 14 weight percent to about 20 weight percent).

In an embodiment, a method of preparing a liquid crystal blue phase comprises: providing a thin-film comprising a mixture of a chiral nematic liquid crystal host and at least one bent-shape compound; heating the thin-film; and cooling the thin-film to produce a liquid blue phase, wherein the liquid crystal blue phase has a stable temperature range of at least about 5° C.

In an embodiment, a method of preparing a liquid crystal blue phase comprises: providing a thin-film comprising a mixture of a chiral nematic liquid crystal host and at least one bent-shape compound; heating the thin-film; and cooling the heated thin-film, to produce a liquid blue phase, wherein the thin-film has a thickness of about 0.5 µm to 2 µm.

In embodiments, the mixture may be formed at a temperature sufficient to disperse the components of the mixture. In embodiments, the thin-film may be heated to a temperature where it is in the isotropic phase. In some embodiments, the thin-film may be heated to a temperature of about 70° C. Specific examples of heating temperature include, about 30° C., about 40° C., about 50° C., about 60° C., about 70° C., about 80° C., about 90° C., about 100° C., about 110° C., about 120° C. about 130° C., about 140° C., about 150° C., about 160° C., about 170° C., about 180° C., and ranges between any two of these temperatures. In embodiments, the heated thin-film may be cooled from the isotropic phase to the liquid crystal blue phase. Specific examples of cooling temperatures include about 0° C., about 10° C., about 20° C., about 30° C., about 40° C., about 50° C., about 60° C., about 70° C., about 80° C., about 90° C., about 100° C., about 110° C., about 120° C., and ranges between any two of these temperatures. In some embodiments, the heated thin-film may be cooled from about 70° C. to about 43° C. In embodiments, the heated thin-film may be cooled to any temperature within the liquid crystal blue phase range.

In some embodiments, the liquid crystal blue phase may have a stable temperature range of at least about 2° C., about 5° C., about 10° C., about 15° C., or about 20° C. In some embodiments, the liquid crystal blue phase may have a stable temperature range of about 10° C. to about 30° C. Specific examples of stable temperature ranges include about 5° C., about 10° C., about 20° C., about 30° C., about 40° C., about 50° C., about 60° C., and ranges between any two of these temperature ranges (for example, about 20° C. to about 60° C.). In some embodiments, the liquid crystal blue phase may have stable temperature range that may be improved by adjusting the thickness of the thin-film. In these embodiments, the stable temperature range may vary based on the composition of the thin-film.

In embodiments, the thin-film may have a thickness of about 0.25 µm to about 15 µm. In some embodiments, the thin-film may have a thickness of about 0.5 µm to about 2 µm. In some embodiments, the thin-film may have a thickness of about 0.75 µm to about 1.5 µm. In some embodiments, the thin-film may have a thickness of about 1 µm. Specific examples of thicknesses include about 0.25 µm, about 0.75 µm, about 1 µm, about 1.5 µm, about 2 µm, about 4 µm, about 10 µm, and ranges between any two of these thicknesses (for example, about 0.75 µm to about 1.5 µm). In some embodiments the thickness of thin-film may be modified to improve the stable temperature range of the liquid crystal blue phase. In these embodiments, the thickness may vary based on the composition of thin-film.

The composite materials described herein may be used to improve the fabrication costs and performance of display devices. In an embodiment, a display device may comprise a composite material described in the embodiments above. In embodiments, the composite material may comprise the liquid crystal layer in a liquid crystal display. In some embodiments, the liquid crystal display may be a blue phase mode liquid crystal display. In embodiments, anisotropic alignment layers may not be required, and the refresh rate may be faster than about 100 Hz.

In some embodiments, the chiral nematic liquid crystal host comprises about 60 weight percent to about 70 weight percent eutectic nematic liquid crystals and about 30 weight percent to about 40 weight percent chiral dopant. In some embodiments, the chiral nematic liquid crystal host comprises about 67 weight percent eutectic nematic crystals and about 33 weight percent chiral dopant. In some embodiments, the weight ratio of nematic liquid crystal host to eutectic nematic liquid crystals may be about 1:1, about 3:2, about 2:1, about 7:3, about 3:1 and ranges between any two of these ratios (for example, about 2:1 to about 3:1).

An exemplary eutectic nematic liquid crystal includes compound SLC-9023 commercially available from Slichem Co. Ltd. An exemplary chiral dopant includes compound R811 commercially available from Merck Co. Ltd. Alternate and/or additional eutectic nematic liquid crystals and chiral dopants may be used within the scope of this disclosure.

In some embodiments, the bent-shape compound may have the structure of formula (I): wherein $R_1$ and $R_2$ may each be independently selected from halogens and aliphatic hydrocarbons comprising 1 to 15 carbons, $Ar_1$, $Ar_2$, $Ar_3$, $Ar_4$, and $Ar_5$, may each be independently selected from homocyclic aromatics, substituted homocyclic aromatics, heterocyclic aromatics, substituted heterocyclic aromatics, polycyclic aromatics, and substituted polycyclic aromatics; $X_1$ and $X_2$ may each be independently selected from $CH_2$, O, NH, and S; and $Y_1$ and $Y_3$ may each be independently selected from C=O, C=CH$_2$, C=NH, and C=S. In some embodiments, $Ar_3$ may be a five-membered aromatic heterocycle. In some embodiments, $Ar_1$, $Ar_2$, $Ar_4$, and $Ar_5$, may each be independently selected from six-membered aromatic heterocycles and six-membered aromatic homocycles.

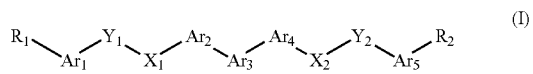

In some embodiments, the bent-shape compound may have the structure of formula (II): wherein $R_3$ and $R_4$ may each be independently selected from halogens and aliphatic hydrocarbons comprising 1 to 15 carbons. In some embodiments, $R_3$ may be $C_7H_{15}$ and $R_4$ may be F, and have the structure (III).

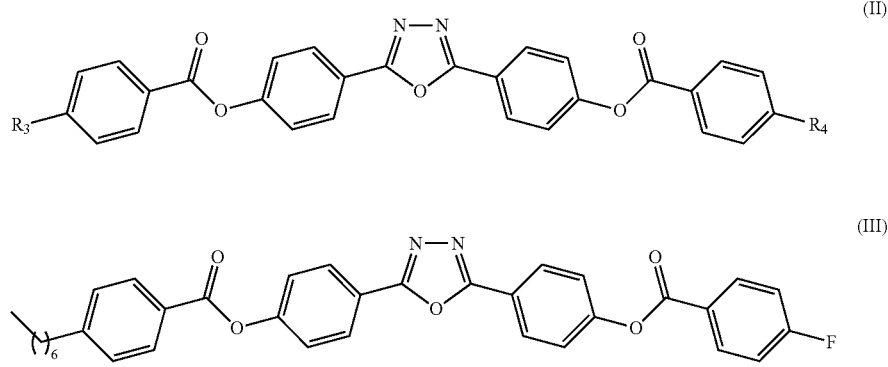

EXAMPLES

Example 1

Fabrication of a Thin-Film, by Spin-Coating

A mixture containing a chiral nematic liquid crystal (N*LC) host (67.2:32.8 by weight ratio of conventional nematic liquid crystals (homemade) to chiral dopant (R811 (Merck, Darmstadt, Germany))) and the bent-shaped molecule (III) as dopant, with the weight ratio of 93:7 was prepared and heated to just above the clearing point of the liquid for 30 minutes. A drop (2 μL) of the mixture was placed onto a quartz substrate settled on the rotor. The rotation was performed at 200 RPM and maintained for 30 seconds minutes. After spin-coating the thin-film was covered by a second substrate without any shifting or pressing. Analysis by scanning electron microscopy (SEM) found that a uniform 1.0 μm-layer was formed.

Example 2

Influence of Thickness on the Blue Phase Range

Thin-films of a mixture containing a chiral nematic liquid crystal (N*LC) host (67.2:32.8 by weight ratio of conventional nematic liquid crystals (homemade) to chiral dopant (R811 (Merck, Darmstadt, Germany))) and the bent-shaped molecule (III) as dopant, with the weight ratio of 93:7 were deposited on quartz substrates at thicknesses of 15.0 μm, 9.5 μm, 5.2 μm, 2.0 μm, 1.0 μm and 0.5 μm. The samples were heated from the chiral nematic phase to the isotropic state, and then cooled to room temperature at the rate of 1° C./min. Thus, the blue phase ranges of the heating and cooling processes were tested (FIG. 1). The blue phase range changed a little when the material layer was thick (from 5.2 to 15.0 μm); however, there was an evident change if the material layer was thin (from 0.5 to 2.0 μm). Interestingly, the blue phase widened up rapidly as the thickness decreased from 5.2 to 1.0 μm and narrowed down as the thickness continually decreased. In addition, it was found that blue phase ranges of the heating process were about 50% narrower than that of the cooling. This may be due to super-cooling of the blue phase during the cooling process.

The maximum blue phase range of about 27° C. was observed for the 1.0 μm-thick sample. This is a dramatic improvement compared to typical blue phase materials which have a stability range of only a few degrees.

Example 3

Blue Phase Liquid Crystal Device

A liquid crystal display device can be fabricated where electrode gap of the in-plane switching (IPS) driver can be about 1 μm thick and filled with a mixture of a chiral nematic liquid crystal (N*LC) host (67.2:32.8 by weight ratio of conventional nematic liquid crystals (homemade) to chiral dopant (R811 (Merck, Darmstadt, Germany))) and the bent-shaped molecule (III) as dopant, with the weight ratio of 93:7. The display device can be fabricated without a surface orientation treatment, and the IPS driver can operate as a blue phase liquid crystal with a stable temperature range of 27° C.

In the present disclosure, reference is made to the accompanying figure, which form a part hereof. The illustrative embodiments described in the detailed description, FIGURE, and claims are not meant to be limiting. Other embodiments may be used, and other changes may be made, without departing from the spirit or scope of the subject matter presented herein. It will be readily understood that the aspects of the present disclosure, as generally described herein, and illustrated in the FIGURE, may be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or FIGURE, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 substituents refers to groups having 1, 2, or 3 substituents. Similarly, a group having 1-5 substituents refers to groups having 1, 2, 3, 4, or 5 substituents, and so forth.

What is claimed is:

1. A composite material comprising:

a chiral nematic liquid crystal host;

at least one bent-shape compound of formula (I):

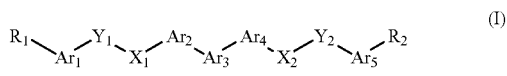

wherein $R_1$ and $R_2$ are each independently selected from halogens and aliphatic hydrocarbons comprising 1 to 15 carbons;

$Ar_1, Ar_2, Ar_3, Ar_4,$ and $Ar_5,$ are each independently selected from optionally substituted homocyclic, heterocyclic, and polycyclic aromatics;

$X_1$ and $X_2$ are each independently selected from $CH_2$, O, NH, and S;

$Y_1$ and $Y_2$ are each independently selected from C=O, C=CH$_2$, C=NH, and C=S; and wherein the composite material has a thickness of about 0.25 μm to about 10 μm and wherein the composite material has a liquid crystal blue phase.

2. The composite material of claim 1, wherein the composite material has a thickness of about 1 μm.

3. The composite material of claim 1, wherein the liquid crystal blue phase of the composite material has a stable temperature range of at least about 10° C.

4. The composite material of claim 1, wherein $X_1$ and $X_2$ are each O, and wherein $Y_1$ and $Y_2$ are each C=O.

5. The composite material of claim 1, wherein $Ar_3$ is a five-membered aromatic heterocycle.

6. The composite material of claim 1, wherein $Ar_1$, $Ar_2$, $Ar_4$, and $Ar_5$, are each independently selected from six-membered aromatic heterocycles and homocycles.

7. The composite material of claim 1, wherein the bent-shape compound has the structure of formula (II):

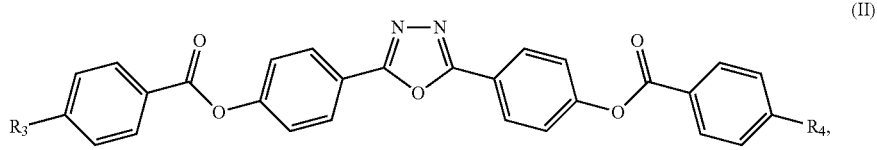

(II)

wherein $R_3$ and $R_4$ are each independently selected from halogens and aliphatic hydrocarbons comprising 1 to 15 carbons.

8. The composite material of claim 7, wherein $R_3$ is $C_7H_{15}$ and $R_4$ is F.

9. The composite material of claim 1, wherein the bent-shape compound is present at about 5 weight percent to about 20 weight percent.

10. The composite material of claim 1, wherein the chiral nematic liquid crystal host comprises about 60 weight percent to about 70 weight percent eutectic nematic liquid crystals and about 30 weight percent to about 40 weight percent chiral dopant.

11. A method of preparing a liquid crystal blue phase, the method comprising:
providing a thin-film comprising a mixture of a chiral nematic liquid crystal host and at least one bent-shape compound;
heating the thin-film; and
cooling the heated thin-film, wherein the thin-film has a thickness of about 0.25 μm to 10 μm to produce a liquid crystal blue phase.

12. The method of claim 11, wherein heating the thin-film comprises heating the thin-film having a thickness of about 1 μm.

13. The method of claim 11, wherein cooling the heated thin-film comprises cooling the heated thin-film to produce the liquid crystal blue phase, wherein the liquid crystal blue phase has a stable temperature range of at least about 10° C.

14. The method of claim 11, wherein providing the thin-film comprises providing the thin-film comprising the mixture of the chiral nematic liquid crystal host and at least one bent-shape compound having the structure of formula (I):

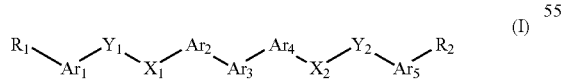

(I)

wherein $R_1$ and $R_2$ are each independently selected from halogens and aliphatic hydrocarbons comprising 1 to 15 carbons;
$Ar_1, Ar_2, Ar_3, Ar_4,$ and $Ar_5,$ are each independently selected from optionally substituted homocyclic, heterocyclic, and polycyclic aromatics;
$X_1$ and $X_2$ are each independently selected from $CH_2$, O, NH, and S; and $Y_1$ and $Y_2$ are each independently selected from C=O, C=CH$_2$, C=NH, and C=S.

15. The method of claim 14, wherein providing the thin-film comprises providing the thin-film comprising the mixture of the chiral nematic liquid crystal host and at least one bent-shape compound having the structure of formula (I), wherein $Ar_3$ is a five-membered aromatic heterocycle.

16. The method of claim 14, wherein providing the thin-film comprises providing the thin-film comprising the mixture of the chiral nematic liquid crystal host and at least one bent-shape compound having the structure of formula (I), wherein $Ar_1$, $Ar_2$, $Ar_4$, and $Ar_5$, are each independently selected from six-membered aromatic heterocycles and homocycles.

17. The method of claim 11, wherein providing the thin-film comprises providing the thin-film comprising the mixture of the chiral nematic liquid crystal host and at least one bent-shape compound having the structure of formula (II):

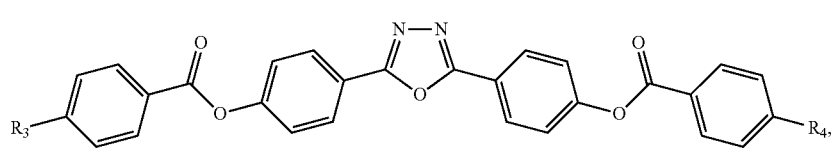

(II)

wherein $R_3$ and $R_4$ are each independently selected from halogens and aliphatic hydrocarbons comprising 1 to 15 carbons.

18. The method of claim 17, wherein providing the thin-film comprises providing the thin-film comprising the mixture of the chiral nematic liquid crystal host and at least one bent-shape compound having the structure of formula (II), wherein $R_3$ is $C_7H_{15}$ and $R_4$ is F.

19. The method of claim 11, wherein heating the thin-film comprises heating to a temperature above a clearing point of the thin-film; and cooling the heated thin-film comprises cooling at about 1° C. per minute.

20. A display device comprising a composite material, wherein the composite material comprises:
a chiral nematic liquid crystal host;
at least one bent-shape compound of formula (I):

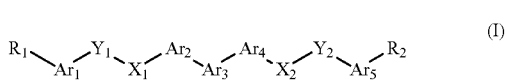

(I)

wherein $R_1$ and $R_2$ are each independently selected from halogens and aliphatic hydrocarbons comprising 1 to 15 carbons;
$Ar_1, Ar_2, Ar_3, Ar_4$ and $Ar_5,$ are each independently selected from optionally substituted homocyclic, heterocyclic, and polycyclic aromatics;
$X_1$ and $X_2$ are each independently selected from $CH_2$, O, NH, and S;

$Y_1$ and $Y_2$ are each independently selected from C=O, C=CH$_2$, C=NH, and C=S; and wherein the composite material is configured as a thin-film having a thickness of about 0.25 μm to about 10 μm, and wherein a liquid crystal blue phase of the composite material has a stable temperature range of at least about 5° C.

21. The composite material of claim 1, wherein the composite material has a thickness of about 0.5 μm to about 2 μm.

22. The method of claim 11, wherein providing the thin-film comprises providing the thin-film comprising the mixture of the chiral nematic liquid crystal host and at least one bent-shape compound, wherein the thin-film has a thickness of about 0.5 μm to about 2 μm.

23. The display device of claim 20, wherein the thin-film has a thickness of about 0.5 μm to about 2 μm.

* * * * *